US012611526B2

(12) United States Patent
    Koga et al.

(10) Patent No.:  US 12,611,526 B2
(45) Date of Patent:     Apr. 28, 2026

(54) METHOD FOR PRODUCING BALLOON CATHETER

(71) Applicant: KANEKA CORPORATION, Osaka (JP)

(72) Inventors: Yojiro Koga, Settsu (JP); Masahiro Kojima, Settsu (JP); Yoshinori Nakano, Settsu (JP); Masato Tsueda, Settsu (JP)

(73) Assignee: KANEKA CORPORATION, Osaka (JP)

( * ) Notice: Subject to any disclaimer, the term of this patent is extended or adjusted under 35 U.S.C. 154(b) by 1075 days.

(21) Appl. No.: 17/640,882

(22) PCT Filed: Aug. 24, 2020

(86) PCT No.: PCT/JP2020/031828
    § 371 (c)(1),
    (2) Date: Mar. 7, 2022

(87) PCT Pub. No.: WO2021/049282
    PCT Pub. Date: Mar. 18, 2021

(65) Prior Publication Data
    US 2022/0323728 A1      Oct. 13, 2022

(30) Foreign Application Priority Data

Sep. 9, 2019    (JP) ................................. 2019-163858

(51) Int. Cl.
    *B29C 67/00*        (2017.01)
    *A61M 25/10*        (2013.01)
(52) U.S. Cl.
    CPC ............................... *A61M 25/1029* (2013.01)

(58) Field of Classification Search
    CPC .................................................. A61M 25/1029
    See application file for complete search history.

(56)                References Cited

U.S. PATENT DOCUMENTS 5,209,799  A  *  5/1993  Vigil ................. A61M 25/1038
                                                       604/271
    5,336,234  A     8/1994  Vigil et al.
                    (Continued)

FOREIGN PATENT DOCUMENTS

JP          5-293174  A      11/1993
    JP       2006271678  A  *  10/2006   ........ A61M 25/1038
                    (Continued)

OTHER PUBLICATIONS

International Search Report, issued in PCT/JP2020/031828, mailed Sep. 29, 2020.

*Primary Examiner* — Nicholas Krasnow
(74) *Attorney, Agent, or Firm* — Birch, Stewart, Kolasch & Birch, LLP

(57)                ABSTRACT

The method for producing a balloon catheter comprises a tubular object preparing step to prepare a tubular object having a space extending in the distal-proximal direction, a balloon preparing step to prepare a balloon, a balloon placement step to place the balloon in the tubular object and inflate the balloon, and a balloon deflating step to deflate the balloon and form a wing-shaped portion, wherein a projecting portion is placed on within a mean circle C1 centered at a center P1 of the tubular object, and a radius of the mean circle C1 is an average value of a shortest distance D1 from the center P1 of the tubular object to an inside surface P2 of the tubular object and a longest distance D2 from the center P1 of the tubular object to the inside surface P3 of the tubular object on a cross-section in the balloon placement step.

20 Claims, 7 Drawing Sheets

(56)    References Cited

U.S. PATENT DOCUMENTS

| | | | | |
|---|---|---|---|---|
| 5,350,361 A * | 9/1994 | Tsukashima | ...... A61M 25/1002 | |
| | | | | 264/DIG. 41 |
| 5,759,172 A * | 6/1998 | Weber | ............... A61M 25/1002 | |
| | | | | 604/525 |
| 5,783,227 A * | 7/1998 | Dunham | .................. B29C 53/08 | |
| | | | | 425/395 |
| 6,283,743 B1 * | 9/2001 | Traxler | ............. A61M 25/1038 | |
| | | | | 264/209.3 |
| 7,951,164 B2 * | 5/2011 | McMorrow | ....... A61M 25/1038 | |
| | | | | 606/191 |
| 7,972,351 B2 * | 7/2011 | Trinidad | ........... A61M 25/1002 | |
| | | | | 606/167 |
| 2001/0047149 A1 * | 11/2001 | Traxler | ............. A61M 25/1038 | |
| | | | | 264/209.3 |
| 2006/0091585 A1 | 5/2006 | Kelley | | |
| 2007/0060863 A1 | 3/2007 | Goeken et al. | | |
| 2007/0112300 A1 * | 5/2007 | Roman | ................... B29C 49/04 | |
| | | | | 264/239 |
| 2017/0007805 A1 | 1/2017 | Tsubooka | | |
| 2018/0043140 A1 | 2/2018 | Iwano et al. | | |
| 2021/0077790 A1 | 3/2021 | Iwano et al. | | |

FOREIGN PATENT DOCUMENTS

| | | | | |
|---|---|---|---|---|
| JP | 2009-508576 A | | 3/2009 | |
| JP | 2014140462 A | * | 8/2014 | |
| JP | 2017-12678 A | | 1/2017 | |
| JP | 2018-27166 A | | 2/2018 | |
| WO | WO 2016/163495 A1 | | 10/2016 | |

* cited by examiner

【FIG. 1】
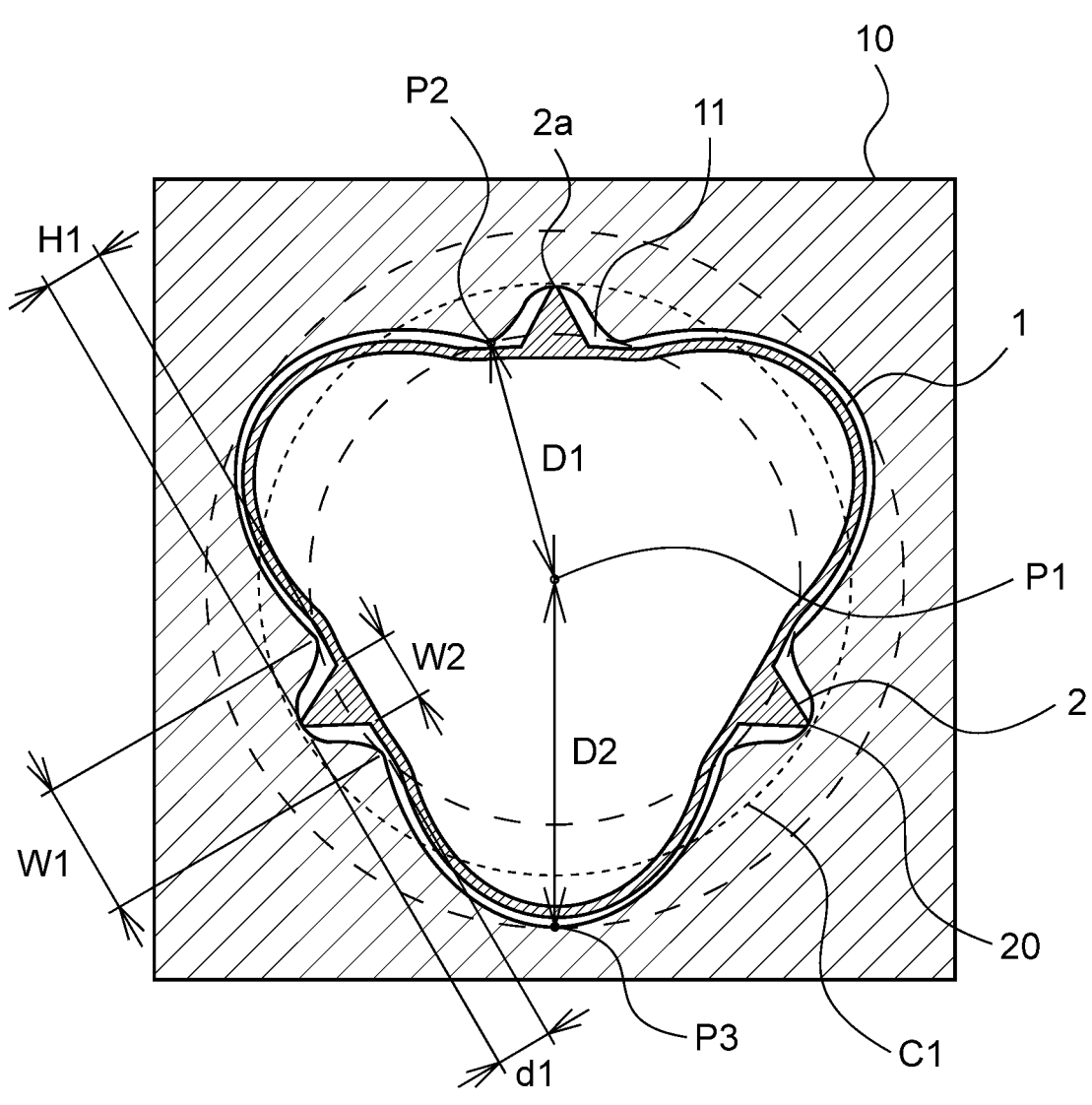

【FIG. 2】
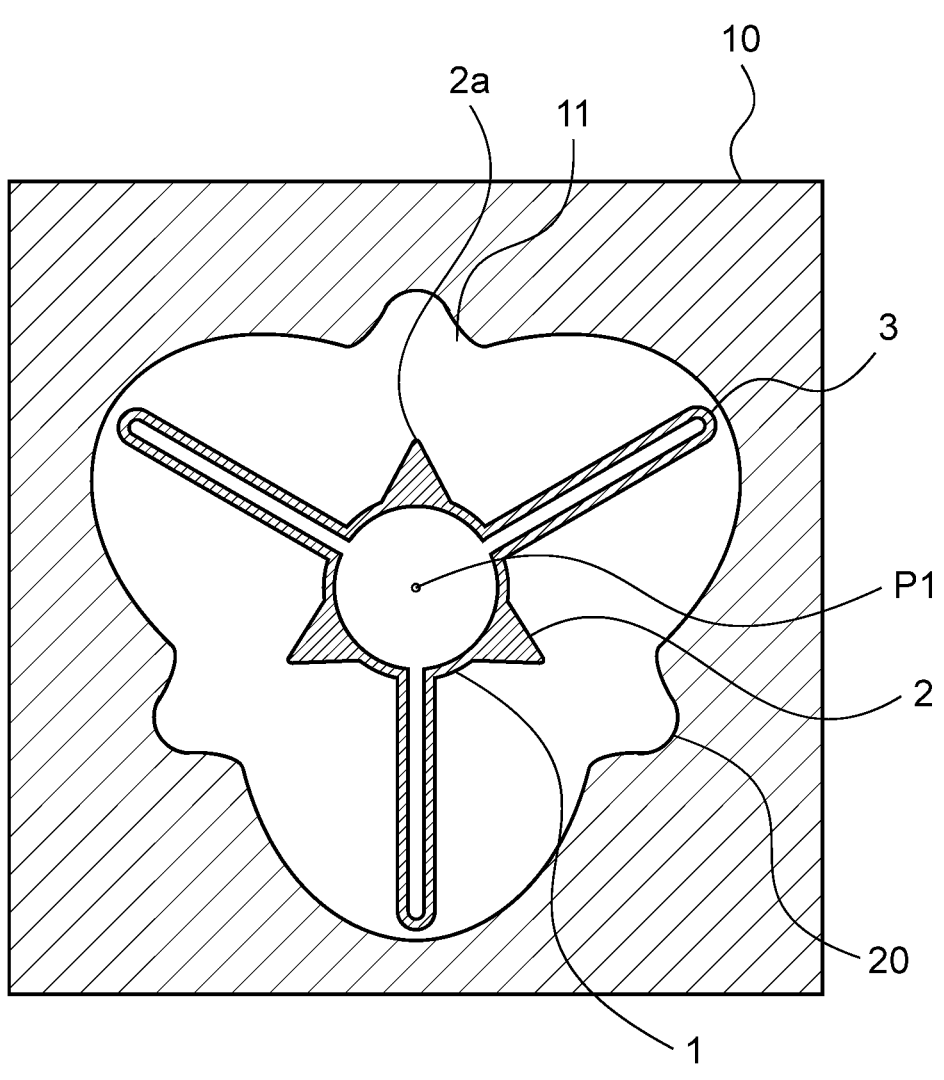

【FIG. 3】
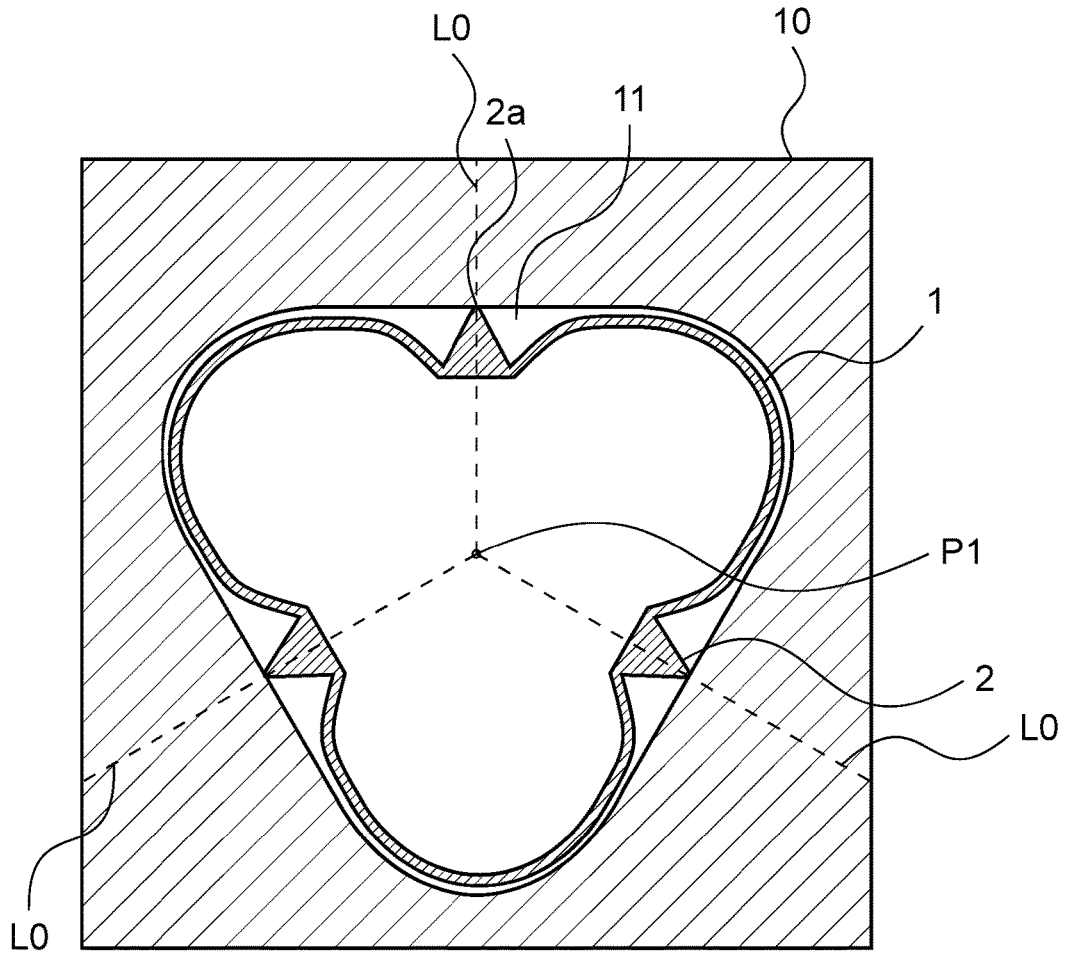

【FIG. 4】
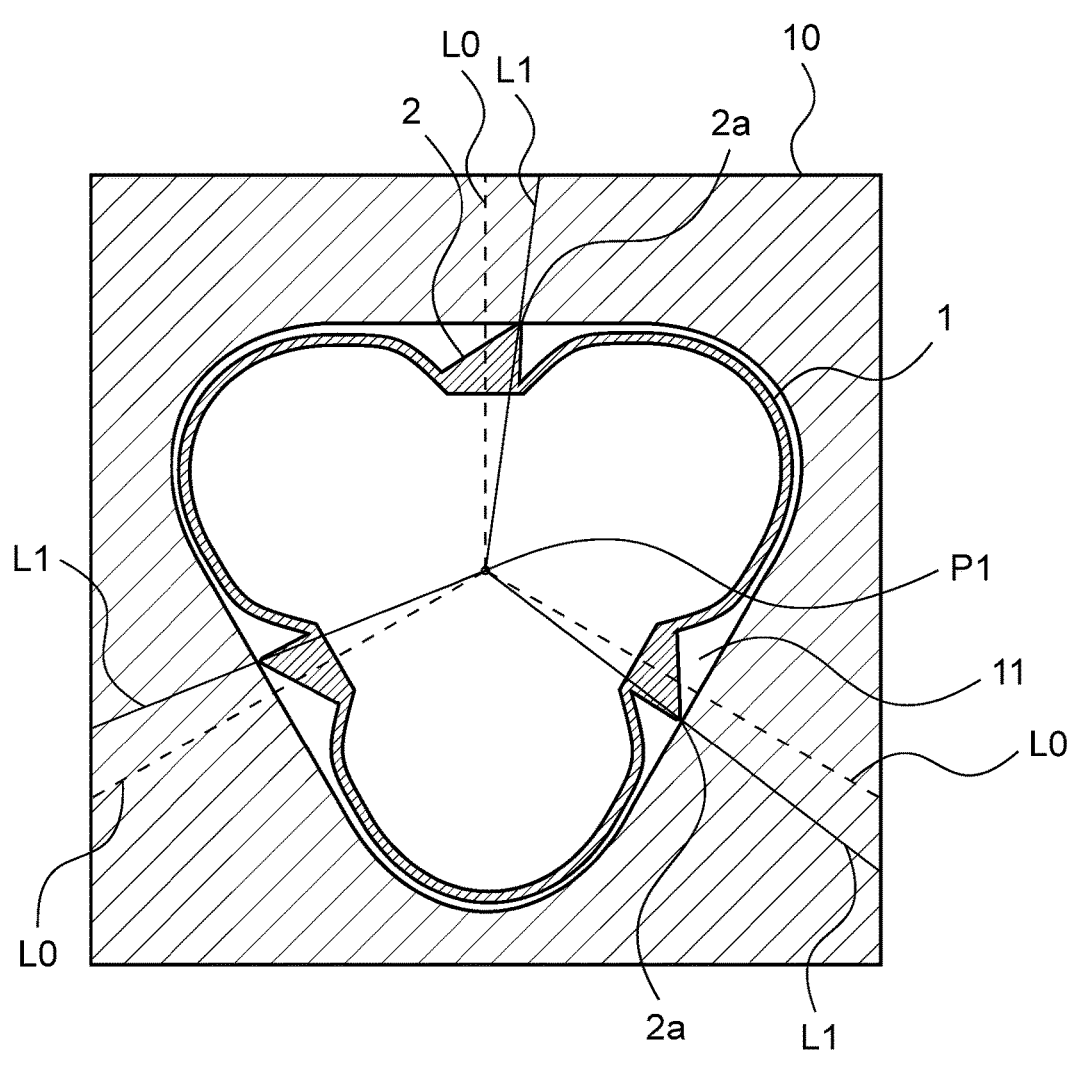

【FIG. 5】
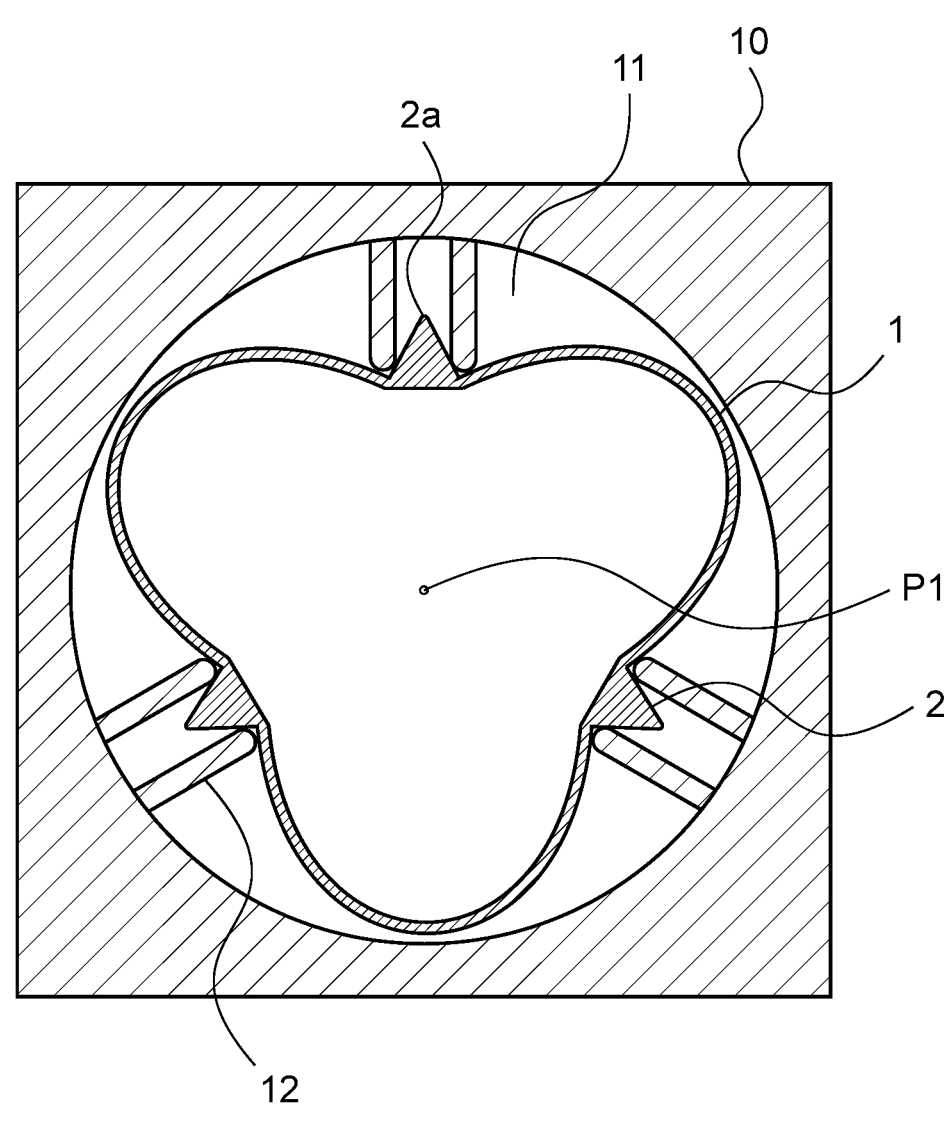

【FIG. 6】
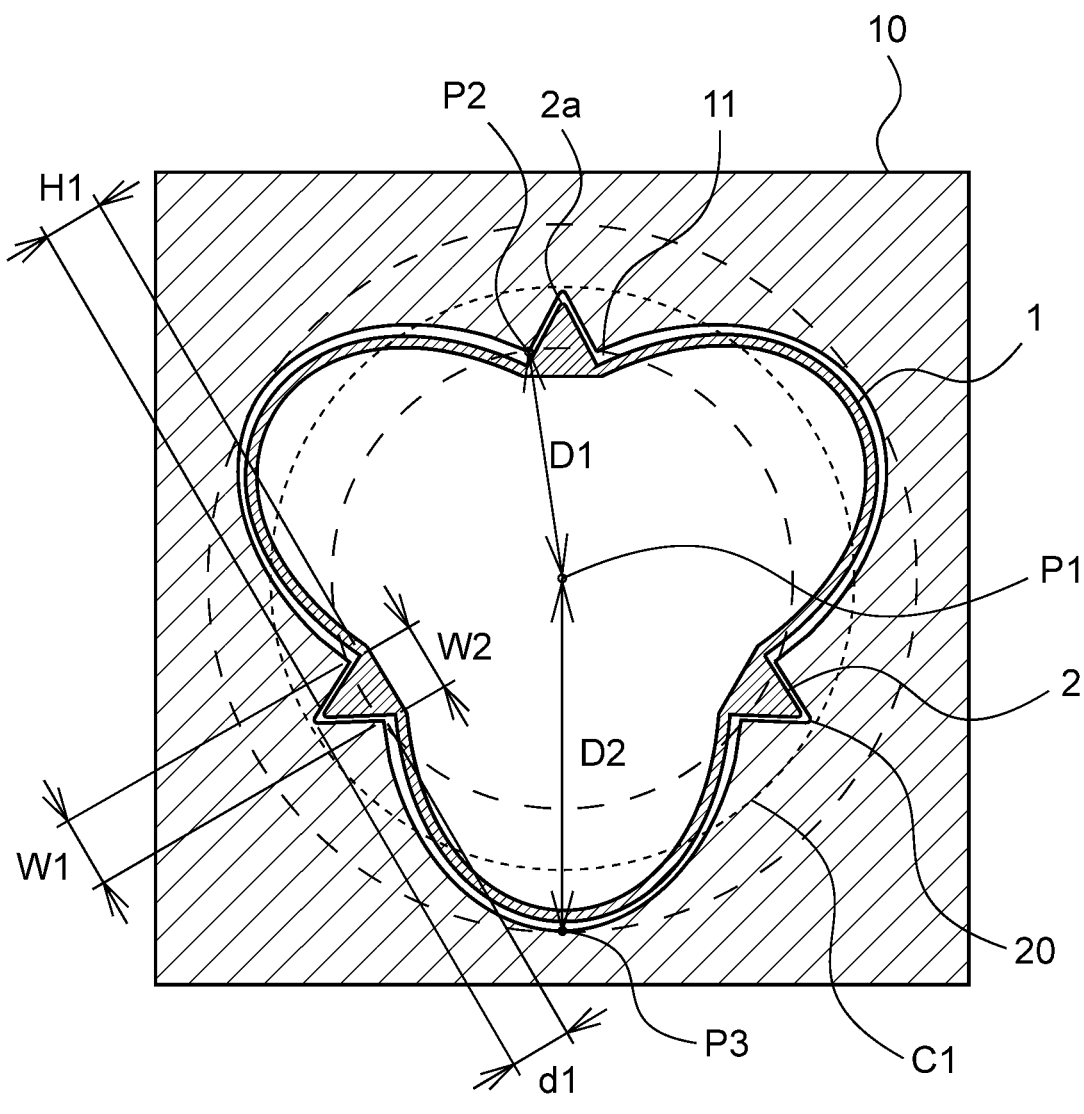

【FIG. 7】
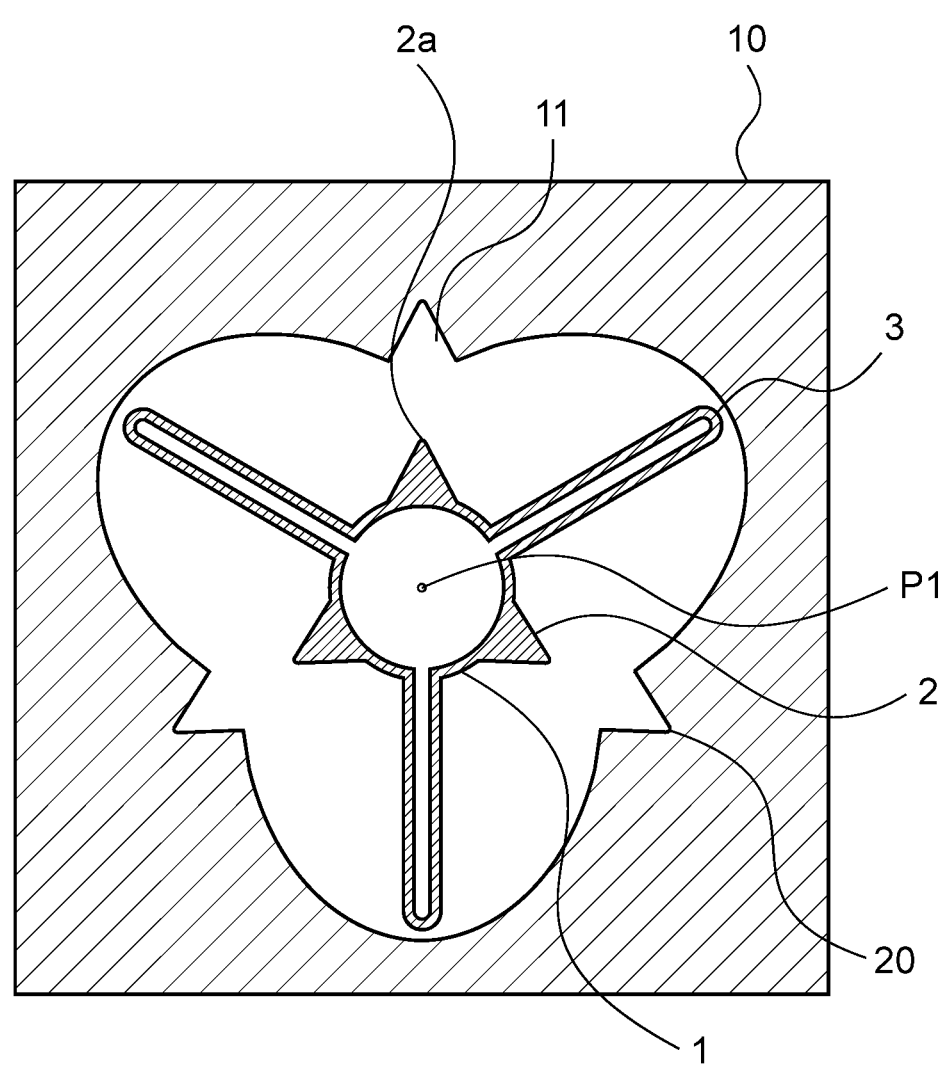

METHOD FOR PRODUCING BALLOON CATHETER

TECHNICAL FIELD

The present invention relates to a method for producing a balloon catheter having a balloon provided with a projecting portion.

BACKGROUND ART

It is known that various diseases are caused due to stagnation of blood circulation by stenosis of a blood vessel, which is a flow path for blood circulation in the body. In particular, when the arteria coronaria for supplying blood to the heart becomes stenosed, a severe disease such as angina and myocardial infarction may be produced. Angioplasty such as PTA and PTCA is known as a method for treating a stenosis part of a blood vessel. A balloon catheter is used for expanding a stenosis part in angioplasty. Angioplasty has been widely carried out, since angioplasty is low-invasive therapy without thoracotomy unlike bypass surgery.

A stenosis part hardened by calcification or the like may be formed on the inner wall of the blood vessel in some cases. It is difficult to dilate a stenosis part in such a calcified lesion with a general balloon catheter. A method for dilating a stenosis part by placing an indwelling vasodilating instrument referred to as stent is also used, but ISR: In-Stent-Restenosis may occur after such a treatment in some cases. ISR means that angiostenosis may be caused again due to excessive growth of neointima of a blood vessel. Neointima is soft and the surface is slippery at an ISR lesion; as a result, a blood vessel may be hurt by moving the place of a balloon from the lesion in some cases in a case where a general balloon catheter is used and the balloon is inflated.

A balloon catheter having a balloon with a scoring element is known as a balloon catheter that can dilate a stenosis part even at such a calcified lesion and an ISR lesion (For example, Patent Documents 1 to 5).

PRIOR ART DOCUMENT

Patent Document

Patent document 1: JP 2018-27166 A
Patent document 2: WO 2016/163495
Patent document 3: JP 2017-12678 A
Patent document 4: JP 2009-508576 T
Patent document 5: JP H5-293174 A

SUMMARY OF THE INVENTION

Problems to be Solved by the Invention

In general, a balloon of a balloon catheter is covered with a cylindrical tube having a slightly larger inner diameter than an outer diameter of the folded balloon as a protective tube in order to protect the folded balloon until the time of use. The folded balloon of the balloon catheter equipped with a scoring element, described in Patent documents 1 to 5, may be similarly covered with a protective tube, but it is difficult to neatly fold a balloon equipped with a scoring element. Thus, there is a problem that the folded balloon becomes difficult to be inserted into a protective tube due to larger outer diameter. In addition, there is a problem that the balloon easily becomes enlarged and the outer diameter becomes larger when the balloon is taken out from the protective tube for use, as a result, the passing performance of the balloon catheter through a blood vessel becomes worse. Furthermore, it is difficult to control the position of a scoring element in the folded balloon, since the balloon is difficult to be neatly folded. As a result, the individual difference in the fixing force of the balloon to a stenosed vessel becomes larger, when the balloon is inflated.

In addition, when the balloon catheter equipped with a scoring element is folded, the scoring element may be crushed in some cases. When the scoring element is crushed, the balloon may easily slip from a stenosis part of a blood vessel in the case where the balloon is inflated and thus the displacement of the balloon may be caused.

The present invention was completed in view of the above circumstances, and the objective thereof is to provide a method for producing a balloon catheter. The balloon has a projecting portion on an outer surface and can be neatly folded with controlling the position of the projecting portion. In addition, when the balloon is folded, the projecting portion is hardly crushed.

Solutions to the Problems

A first method for producing a balloon catheter to solve the above problems is characterized in that the balloon catheter comprises a shaft and a balloon, the shaft extends in a distal-proximal direction, and the balloon provided on a distal side of the shaft and has a projecting portion on an outer surface, the method comprises: a tubular object preparing step to prepare a tubular object internally having a space extending in the distal-proximal direction, a balloon preparing step to prepare the balloon, a balloon placement step to placing the balloon in the tubular object and inflate the balloon by pressurizing an inside of the balloon, and a balloon deflating step to deflate the balloon and form a wing-shaped portion by depressurizing the inside of the balloon, wherein the projecting portion is placed on the inside of a mean circle centered at a gravity center of the tubular object, and a radius of the mean circle is an average value of a shortest distance from the gravity center of the tubular object to an inside surface of the tubular object and a longest distance from the gravity center of the tubular object to the inside surface of the tubular object on a cross-section perpendicular to the distal-proximal direction of the tubular object in the balloon placement step.

The method for producing a balloon catheter according to the present invention preferably further comprises an apex-pressing step to press an apex part of the projecting portion inward of the tubular object after the balloon placement step.

It is preferred in the method for producing a balloon catheter according to the present invention that the balloon has a plurality of the projecting portions, and a straight line through the gravity center of the tubular object and the apex part of the projecting portion turns round an axis direction of the tubular object and circling directions of the all straight lines through the gravity center of the tubular object and the apex parts of the projecting portions are the same on the cross-section perpendicular to the distal-proximal direction of the tubular object in the apex-pressing step.

It is preferred in the method for producing a balloon catheter according to the present invention that the tubular object has a plurality of groove portions extending in the distal-proximal direction at inside the tubular object, a width of the groove portion is larger than a width of the projecting portion, and a depth of the groove portion is smaller than a height of the projecting portion, the groove portion is positioned within the mean circle, and the method comprises an apex-positioning step to position the projecting portion inside of the groove portion after the balloon placement step.

The method for producing a balloon catheter according to the present invention preferably comprises a projecting portion both sides-pressing step to press both sides of the projecting portion to an inside of the tubular object on the cross-section perpendicular to the distal-proximal direction after the balloon placement step.

It is preferred in the method for producing a balloon catheter according to the present invention that the tubular object has a plurality of groove portions extending in the distal-proximal direction at inside the tubular object, a width of the groove portion is smaller than a width of the projecting portion, and a depth of the groove portion is larger than a height of the projecting portion, the groove portion is positioned within the mean circle, and the step comprises an apex-positioning step to position the apex part inside of the groove portion after the balloon placement step.

A second method for producing a balloon catheter to solve the above problems is characterized in that the balloon catheter comprises a shaft and a balloon, the shaft extends in a distal-proximal direction, and the balloon provided on a distal side of the shaft and has a projecting portion on an outer surface, the method comprises: a tubular object preparing step to prepare a tubular object internally having a space extending in the distal-proximal direction and having a plurality of groove portions extending in the distal-proximal direction, a balloon preparing step to prepare the balloon, a balloon placement step to placing the balloon in the tubular object and inflate the balloon by pressurizing an inside of the balloon, and a balloon deflating step to deflate the balloon and form a wing-shaped portion by depressurizing the inside of the balloon, wherein the projecting portion is placed on the inside of a mean circle centered at a gravity center of the tubular object, and a radius of the mean circle is an average value of a shortest distance from the gravity center of the tubular object to an inside surface of the tubular object and a longest distance from the gravity center of the tubular object to the inside surface of the tubular object on a cross-section perpendicular to the distal-proximal direction of the tubular object in the balloon placement step, and wherein the projecting portion is positioned inside of the groove portion in the balloon placement step.

It is preferred in the method for producing a balloon catheter according to the present invention that a difference between a width of the groove portion and a width of the projecting portion is 50% or lower, comprising 0%, of the width of the projecting portion on the cross-section perpendicular to the distal-proximal direction of the tubular object.

It is preferred in the method for producing a balloon catheter according to the present invention that the groove portion is positioned inside of the mean circle.

It is preferred in the method for producing a balloon catheter according to the present invention that the number of the projecting portion is two or more, and the number of the groove portion is the same as the number of the projecting portion.

It is preferred in the method for producing a balloon catheter according to the present invention that the projecting portion is composed of the same material of a main body of the balloon.

It is preferred in the method for producing a balloon catheter according to the present invention that the balloon has hydrophilic coating on an outer surface, and the method comprises a coating removing step to remove the hydrophilic coating on the apex part of the projecting portion.

It is preferred in the method for producing a balloon catheter according to the present invention that the coating removing step is carried out after the balloon placement step, and the balloon is slid in the distal-proximal direction with contacting an outer surface of the projecting portion with an inner surface of the tubular object in the coating removing step.

Effect of the Invention

In accordance with the method for producing a balloon catheter according to the present invention, the balloon can be folded with controlling the position of the projecting portion while the projecting portion is hardly crushed by positioning the projecting portion on the inside of a mean circle centered at a gravity center of the tubular object, and having a radius of an average value of a shortest distance from the gravity center of the tubular object to an inside surface of the tubular object and a longest distance from the gravity center of the tubular object to the inside surface of the tubular object on a cross-section perpendicular to the distal-proximal direction of the tubular object in the balloon placement step to placing the balloon in the tubular object and to inflate the balloon by pressurizing the inside of the balloon.

BRIEF DESCRIPTION OF THE DRAWINGS

FIG. 1 is a cross-sectional view perpendicular to the distal-proximal direction of the tubular object in the balloon placement step of the first production method in the embodiment of the present invention.

FIG. 2 is a cross-sectional view perpendicular to the distal-proximal direction of the tubular object in the balloon deflating step of the first production method in the embodiment of the present invention.

FIG. 3 is a cross-sectional view perpendicular to the distal-proximal direction of the tubular object in the apex-pressing step of the first production method in the other embodiment of the present invention.

FIG. 4 is a cross-sectional view perpendicular to the distal-proximal direction of the tubular object in the apex-pressing step of the first production method in the further other embodiment of the present invention.

FIG. 5 is a cross-sectional view perpendicular to the distal-proximal direction of the tubular object in the projecting portion both sides-pressing step of the first production method in the other embodiment of the present invention.

FIG. 6 is a cross-sectional view perpendicular to the distal-proximal direction of the tubular object in the balloon placement step of the second production method in the embodiment of the present invention.

FIG. 7 is a cross-sectional view perpendicular to the distal-proximal direction of the tubular object in the balloon deflating step of the second production method in the embodiment of the present invention.

MODE FOR CARRYING OUT THE INVENTION

Hereinafter, the present invention is described in more detail with the following embodiments. The present invention is however not restricted to the following embodiments in any way, and it is possible to work the present invention according to the embodiments with an additional appropriate change within the range of the above descriptions and the following descriptions. Such a changed embodiment is also included in the technical scope of the present invention. Hatching, member symbol or the like may be conveniently abbreviated in each figure in some cases. The specification and the other figure may be referred in such a case. The size of various members in the figures may be different from the actual size in some cases, since priority is given to contributing to the understanding of the feature of the present invention.

First, the first method for producing a balloon catheter according to the present invention is described.

FIG. 1 is a cross-sectional view in the balloon placement step of the first method for a balloon catheter in the embodiment of the present invention, and FIG. 2 is a cross-sectional view in the balloon deflating step. The first method for producing a balloon catheter is a method for producing a balloon catheter comprising a shaft and a balloon 1, wherein the shaft extends in a distal-proximal direction, and the balloon 1 is placed on a distal side of the shaft and has a projecting portion 2 on an outer surface. The method comprises the tubular object preparing step to prepare a tubular object 10 internally having a space 11 extending in the distal-proximal direction, the balloon preparing step to prepare the balloon 1, the balloon placement step to placing the balloon 1 in the tubular object 10 and inflate the balloon 1 by pressurizing an inside of the balloon 1, and the balloon deflating step to deflate the balloon 1 and form a wing-shaped portion 3 by depressurizing the inside of the balloon 1.

In the present invention, the distal side means the direction of the treatment subject side with respect to the extending direction of the balloon 1, and the near side means the opposite side of the distal side, that is, the direction toward a side of a user, i.e. an operator, with respect to the extending direction of the balloon 1. The direction from the near side to the distal side of the balloon 1 is referred to as the distal-proximal direction.

The balloon catheter is built so that fluid is supplied to the inside of the balloon 1 through the shaft, and the inflation and the deflation of the balloon 1 can be controlled by using an indeflator (balloon pressurizer). The fluid may be pressurized fluid pressurized by a pump or the like.

The shaft extends in the distal-proximal direction and internally has a flow path for fluid. The shaft preferably has a pass for inserting a guide wire internally. For example, the shaft has an outer tube and an inner tube, the inner tube functions as a path for inserting a guide wire, and a space between the inner tube and the outer tube functions as a flow path for fluid as the constitution of the shaft internally having a flow path for fluid and a path for inserting a guide wire. When the shaft has an outer tube and an inner tube, it is preferred that the inner tube extends from the distal edge of the outer tube and penetrates the balloon 1 in the distal-proximal direction, the distal side of the balloon 1 is bound to the inner tube, and the near side of the balloon 1 is bound to the outer tube.

The present invention can be applied to any one of a so-called over-the-wire type balloon catheter and a so-called rapid exchange type balloon catheter. A wire is inserted through from the distal side to the near side of the shaft of an over-the-wire type balloon catheter, and a wire is inserted halfway from the distal side to the near side of the shaft of a rapid exchange type balloon catheter. When the balloon catheter is an over-the-wire type, there is a hub on the near side of the shaft to supply fluid to the shaft though such a hub is not shown in Figures. The hub preferably has a fluid injection part directly connecting to the path of the fluid supplied to the inside of the balloon 1 and a guide wire-inserting part directly connecting the path for inserting a guide wire. When the balloon catheter has the hub equipped with the fluid injection part and the guide wire-inserting part, the balloon 1 becomes easy to be inflated by supplying fluid to the inside of the balloon 1 and deflated, and the balloon catheter can be easily delivered to a treatment target region along the guide wire.

The shaft and the hub can be connected by, for example, adhesion using an adhesive, welding or the like. In particular, the shaft and the hub are preferably connected by adhesion. When the raw material of the shaft and the raw material of the hub are different, for example, the shaft is composed of a highly limp material and the hub is composed of a highly stiff material, and the shaft and the hub are bonded, the connection strength between the shaft and the hub can be improved. As a result, the durability of the balloon catheter can be improved.

An example of the material of the shaft includes polyamide resin, polyester resin, polyurethane resin, polyolefin resin, fluorine resin, vinyl chloride resin, silicone resin and natural rubber. Only one of the materials may be used, or two or more thereof may be used in combination. The material of the shaft is preferably at least one of polyamide resin, polyolefin resin and fluorine resin. When the material of the shaft is at least one of polyamide resin, polyolefin resin and fluorine resin, the sliding performance of the surface of the shaft can be improved and the insertability of the balloon catheter into a blood vessel can be improved.

The balloon 1 is provided on the distal side of the shaft. For example, the balloon 1 and the shaft can be connected by adhesion by an adhesive or welding, or a ring element is fixed at a portion where the end of the balloon 1 and the shaft are overlapped to be swaged. In particular, the balloon 1 and the shaft are preferably connected by welding. When the balloon 1 and the shaft are welded, it becomes difficult to disconnect the balloon 1 and the shaft even when the balloon is repeatedly inflated and deflated. Thus, the connection strength between the balloon 1 and the shaft can be easily improved.

The balloon 1 preferably has a straight tube part, a near side tapered part connected to the near side of the straight tube part, and a distal side tapered part connected to the distal side of the straight tube part. It is preferred that the near tapered part and the distal tapered part are formed so as to reduce the diameter thereof as the distance from the straight tube part increases. When the balloon 1 has a straight tube part, the straight tube part is sufficiently contacted with the constriction part and thus the constriction part can be easily expanded. Further, when the balloon 1 has a near side tapered part and a distal side tapered part of which outer diameters become smaller as the distance from the straight tube part is increased, the outer diameters of the distal end part and the near end part of the balloon 1 can be reduced and thus the step between the shaft and the balloon 1 can be reduced in the case where the balloon 1 is deflated and wound around the shaft. As a result, it becomes easy to insert the balloon 1 in the distal-proximal direction. The inflatable portion is regarded as the balloon 1 in the present invention.

An example of the material of the balloon 1 includes a polyolefin resin such as polyethylene, polypropylene and an ethylene-propylene copolymer; a polyester resin such as polyethylene terephthalate and a polyester elastomer; a polyurethane resin such as polyurethane and a polyurethane elastomer; a polyphenylenesulfide resin; a polyamide resin such as a polyamide elastomer, nylon 6, nylon 6/6, nylon 6/10 and nylon 12; a fluorine resin; a silicone resin; and a natural rubber such as latex rubber. Only one of the materials may be used, or two or more thereof may be used in combination. In particular, the material of the balloon 1 is preferably a polyamide resin, and more preferably nylon 12. When the material of the balloon 1 is a polyamide resin, the flexibility of the balloon 1 can be improved.

The outer diameter of the balloon 1 is preferably 0.5 mm or more, more preferably 1 mm or more, and even more preferably 1.5 mm or more. When the lower limit of the outer diameter of the balloon 1 is adjusted to the above range, the constriction part of a blood vessel can be sufficiently dilatate. The outer diameter of the balloon 1 is preferably 35 mm or less, more preferably 30 mm or less, and even more preferably 25 mm or less. When the upper limit of the outer diameter of the balloon 1 is adjusted to the above range, it is possible to prevent the outer diameter of the balloon 1 from becoming excessively large.

The length of the balloon 1 in the distal-proximal direction is preferably 5 mm or more, more preferably 10 mm or more, and even more preferably 15 mm or more. When the lower limit of the length of the balloon 1 in the distal-proximal direction is adjusted to the above range, an area of a constriction part that can be dilated at a time can be increased and thus the time required for an operation can be shortened. The length of the balloon 1 in the distal-proximal direction is preferably 300 mm or less, more preferably 200 mm or less, and even more preferably 100 mm or less. When the upper limit of the length of the balloon 1 in the distal-proximal direction is adjusted to the above range, an amount of fluid supplied to the inside of the balloon 1 to be inflated for expanding a constriction part can be reduced and thus a time required for sufficiently inflating the balloon 1 can be shortened.

The thickness of the balloon 1 is preferably 5 μm or more, more preferably 7 μm or more, and further preferably 10 μm or more. When the lower limit of the thickness of the balloon 1 is adjusted to the above range, the strength of the balloon 1 can be improved and thus a constriction part can be sufficiently expanded. The upper limit of the thickness of the balloon 1 can be adjusted depending on the application of the balloon catheter, and can be adjusted to, for example, 100 μm or less, 90 μm or less, and 80 μm or less.

The balloon 1 has the projecting portion 2 on the outer surface as shown in FIG. 1 and FIG. 2. Since the balloon 1 has the projecting portion 2 on the outer surface, a crack can be formed in a calcified and stiffened lesion by the projecting portion 2 and thus the balloon 1 can sufficiently expand the calcified lesion. When the balloon 1 is inflated at an ISR lesion, the projecting portion 2 is easily gotten stuck with a neointima, which is flexible and of which surface is slippery, and thus it becomes difficult to misalign the position of the balloon 1 when an ISR lesion is expanded.

The number of the projecting portion 2 may be one and is preferably plural. In other words, the balloon 1 has a plurality of the projecting portion 2 on the outer surface. When the number of the projecting portion 2 is plural, it becomes easy to crack a lesion hardened by calcification. In addition, it also becomes difficult to misalign the position of the balloon 1 at an ISR lesion.

The projecting portion 2 extends in the distal-proximal direction. The length of the projecting portion 2 in the distal-proximal direction is preferably shorter than the length of the balloon 1 in the distal-proximal direction. When the length of the projecting portion 2 in the distal-proximal direction is shorter than the length of the balloon 1 in the distal-proximal direction, there is a part where the projecting portion 2 is not set in a part of the balloon 1 in the distal-proximal direction, and thus the balloon 1 is easily bent. As a result, it becomes possible to improve the insertability of the balloon catheter in a curved blood vessel or the like.

An example of the material of the projecting portion 2 includes a synthetic resin, a metal or the like. The synthetic resin is exemplified by a polyolefin resin such as polyvinyl chloride, polyethylene, polypropylene and cyclic polyolefin; a polystyrene resin; a polymethylpentene resin such as poly-(4-methylpentene-1); a polycarbonate resin; an acrylate resin; an ABS resin; a polyester resin such as polyethylene terephthalate and polyethylene naphthalate; and an polyamide resin such as a butadiene-styrene copolymer, a polyamide elastomer, nylon 6, nylon 6/6, nylon 6/10 and nylon 12. The metal is exemplified by stainless steel, aluminum, aluminum alloy, titanium, titanium alloy, copper, copper alloy, tantalum and cobalt alloy. Only one of the materials may be used, or two or more thereof may be used in combination. The projecting portion 2 may be formed on the outer surface of the balloon 1 by integral molding with using the same material as the material of the balloon 1, or may be separately formed on the outer surface of the balloon 1 using a different material from the material of the balloon 1.

The tubular object 10 internally having a space portion 11 extending in the distal-proximal direction is prepared in the tubular object preparing step. The balloon 1 can be positioned in the space portion 11 that the tubular object 10 internally has.

An example of the material of the tubular object 10 includes a synthetic resin such as a polycarbonate resin, a polyacetal resin and a fluorine resin; and a metal such as iron, copper and stainless steel. In particular, the material of the tubular object 10 is preferably a metal. When the material of the tubular object 10 is a metal, the strength of the tubular object 10 is increased, and it is possible to increase the pressure applied to the inside of the balloon 1 in the balloon placement step.

The balloon 1 is prepared in the balloon preparing step. Then, the balloon 1 is positioned in the tubular object 10 in the balloon placement step as shown in FIG. 1, and the inside of the balloon 1 is pressurized to inflate the balloon 1.

For example, fluid is supplied into the inside of the balloon 1 as the method for pressurizing the inside of the balloon 1. An example of the fluid includes gas such as air and nitrogen gas and liquid such as pure water and normal saline solution. For example, a pump or the like can be used in order to pressurize the fluid.

When the balloon 1 is inflated by pressurizing the inside of the balloon 1 in the tubular object 10 in the balloon placement step, at least a part of the outer surface of the balloon 1 is preferably contacted with the inner surface of the space portion 11. When at least a part of the outer surface of the balloon 1 is contacted with the inner surface of the space portion 11 in the balloon placement step, it becomes easy to form the wing-shaped portion 3 in the balloon deflating step after the balloon placement step.

As shown in FIG. 1, the projecting portion 2 is placed on the inside of the mean circle C1 centered at the gravity center P1 of the tubular object 10, and a radius of the mean circle C1 is an average value of the shortest distance D1 from the gravity center P1 of the tubular object 10 to an inside surface P2 of the tubular object 10 and a longest distance from the gravity center P1 of the tubular object 10 to the inside surface P3 of the tubular object 10 on a cross-section perpendicular to the distal-proximal direction of the tubular object 10 in the balloon placement step.

The balloon deflating step is carried out after the balloon placement step. As shown in FIG. 2, the inside of the balloon 1 is depressurized and the balloon 1 is deflated to form the wing-shaped portion 3 in the balloon deflating step. The wing-shaped portion 3 means the part at which at least parts of the inner surface of the balloon 1 are contacted with each other in the condition that the balloon 1 is deflated.

When the projecting portion 2 of the balloon 1 is positioned inside of the mean circle C1 in the balloon placement step, the projecting portion 2 can be positioned at a position close to the gravity center P1 of the tubular object 10. When the inside of the balloon 1 is depressurized in the subsequent balloon deflating step, the projecting portion 2 located closer to the gravity center P1 of the tubular object 10 reaches the gravity center P1 of the tubular object 10 in advance of the part of the balloon 1 located farther from the gravity center P1 of the tubular object 10 than the projecting portion 2, and the part of the balloon 1 that does not reach the gravity center P1 of the tubular object 10 at the time becomes the wing-shaped portion 3. As a result, the projecting portion 2 can be arranged between a plurality of wing-shaped portion 3 in the balloon 1 in the deflated state, and thus the balloon 1 can be folded with controlling the position of the projecting portion 2. In addition, since the projecting portion 2 is arranged between a plurality of wing-shaped portion 3, an effect that the projecting portion 2 is hardly crushed in the case where the wing-shaped portion 3 is wound and folded can be obtained.

The time to depressurize the inside of the balloon 1 in the balloon deflating step is preferably shorter than the time to pressurize the inside of the balloon 1 in the balloon placement step. When the time to depressurize the inside of the balloon 1 in the balloon deflating step is adjusted to be shorter than the time to pressurize the inside of the balloon 1 in the balloon placement step, a wrinkle and slack are less likely to occur on the wing-shaped portion 3 and the outer surface of the balloon 1 other than the wing-shaped portion 3, and the balloon 1 can be tidily folded. In addition, when the time to pressurize the inside of the balloon 1 in the balloon placement step is adjusted to be longer than the time to depressurize the inside of the balloon 1 in the balloon deflating step, the balloon 1 can be gradually inflated, and the projecting portion 2 can be prevented from becoming deformed by collision with the inner surface of the tubular object 10.

The number of wing-shaped portion 3 formed in the balloon deflating step may be one and is preferably two or more. When the number of the wing-shaped portion 3 formed in the balloon deflating step is two or more, the length of the wing-shaped portion 3 is less likely to be excessively long. As a result, the balloon 1 can be easily folded neatly.

FIG. 3 shows a cross-sectional view in the apex-pressing step of the first method for producing a balloon catheter in accordance with the other embodiment of the present invention.

The apex-pressing step to press the apex part 2a of the projecting portion 2 inward of the tubular object 10 is preferably carried out after the balloon placement step. For example, the balloon 1 is inflated in the condition that the inner surface of the tubular object 10 is contacted with the apex part 2a of the projecting portion 2 as shown in FIG. 3; or a projecting shape part capable of moving from the outside to the inside of the tubular object 10 is formed on the inner surface of the tubular object 10, and the projecting shape part is moved toward the inside of the tubular object 10 in the condition that the projecting shape part is contacted with the apex part 2a of the projecting portion 2; or a discharge port for fluid such as air is formed at the position of the apex part 2a of the projecting portion 2 in the tubular object 10, and compressed air or the like is injected from the injection hole toward the apex part 2a of the projecting portion 2 in order to press the apex part 2a of the projecting portion 2 inward of the tubular object 10. The apex-pressing step is preferably carried out after the balloon placement step and before the balloon deflating step. When the apex part 2a of the projecting portion 2 is pressed inward of the inside of the tubular object 10, the position of the projecting portion 2 can be further brought closer to the gravity center P1 of the tubular object 10 in the balloon placement step. Thus, the step to form the wing-shaped portion 3 and the balloon 1 is folded by deflating the balloon 1 can be promptly carried out. As a result, the production efficiency of a balloon catheter can be improved.

FIG. 4 shows a cross-sectional view in the apex-pressing step of the first method for producing a balloon catheter in accordance with the further other embodiment of the present invention. As shown in FIG. 4, it is preferred that the balloon 1 has a plurality of projecting portion 2, and the straight line L1 through the gravity center P1 of the tubular object 10 and the apex part 2a of the projecting portion 2 turns round the axis direction of the tubular object 10 by revolving the inflated balloon 1 in one direction and the circling directions of the all straight lines L1 through the gravity center P1 of the tubular object 10 and the apex part 2a of the projecting portion 2 are the same on a cross-section perpendicular to the distal-proximal direction of the tubular object 10 in the apex-pressing step. The phrase, the straight line L1 through the gravity center P1 of the tubular object 10 and the apex part 2a of the projecting portion 2 "turns round" the axis direction of the tubular object 10, means that the straight line L1 through the gravity center P1 of the tubular object 10 and the apex part 2a of the projecting portion 2 undergoes displacement in a circumferential direction around the axis of the tubular object 10 as the straight line L1 heads from the gravity center P1 of the tubular object 10 to the apex part 2a of the projecting portion 2. Specifically, the phrase means that the straight line L1 through the gravity center P1 of the tubular object 10 and the apex part 2a of the projecting portion 2 undergoes displacement in a circumferential direction around the axis along the distal-proximal direction of the tubular object 10 with respect to the straight line L0 through the gravity center P1 of the tubular object 10 and the apex part 2a of the projecting portion 2 before the balloon 1 is rotated in one direction as shown in FIG. 4.

When the straight line L1 through the gravity center P1 of the tubular object 10 and the apex part 2a of the projecting portion 2 turns round the axis direction of the tubular object 10 and circling directions of the all straight lines L1 through the gravity center P1 of the tubular object 10 and the apex part 2a of the projecting portion 2 are the same on a cross-section perpendicular to the distal-proximal direction of the tubular object 10, the projecting portion 2 becomes closer to the gravity center P1 of the tubular object 10 while the projecting portion 2 leans toward the circling direction of the balloon 1. Since the outer diameter of the balloon 1 folded while the projecting portion 2 leans easily becomes small, the low invasiveness of the balloon catheter can be improved. In addition, when the balloon 1 with the leaned projecting portion 2 is inflated for the use of the balloon catheter, the leaned projecting portion 2 is contacted with a lesion and an oblique or helical incision can be made in the lesion. As a result, the expansion force of the balloon catheter can be improved. Furthermore, when the balloon 1 is folded with leaning the projecting portion 2, it becomes difficult to contact the apex part 2a of the projecting portion 2 with the membrane part of the balloon 1. As a result, the balloon can be hardly scratched.

It is preferred in the method for producing a balloon catheter comprising the apex-pressing step that the tubular object 10 internally has a plurality of groove portions 20 extending in the distal-proximal direction at inside the tubular object 10, the width W1 of the groove portion 20 is larger than the width W2 of the projecting portion 2, and the depth d1 of the groove portion 20 is smaller than the height H1 of the projecting portion 2. The method preferably comprises the apex-positioning step to position the apex part 2a inside of the groove portion 20 after the balloon placement step. The groove portion 20 is preferably placed in the inside of the mean circle C1. When the tubular object 10 internally has a plurality of groove portions 20, the width W1 of the groove portion 20 is larger than the width W2 of the projecting portion 2, and the depth d1 of the groove portion 20 is smaller than the height H1 of the projecting portion 2, a load is easily applied to the apex part 2a of the projecting portion 2 by contacting the apex part 2a of the projecting portion 2 with the inner surface of the groove portion 20. When the balloon 1 is rotated while the apex part 2a is placed inside of the groove portion 20 or the balloon 1 is rotated while the apex part 2a is not placed inside of the groove portion 20, the leaned projecting portion 2 is placed inside of the groove portion 20 and thus the balloon 1 can be folded with leaning the projecting portion 2.

When the groove portion 20 is located inside of the mean circle C1, the projecting portion 2 arranged near the gravity center P1 of the tubular object 10 reaches the gravity center P1 of the tubular object 10 in advance of the other part of the balloon 1 in the case where the inside of the balloon 1 is depressurized in the balloon deflating step and thus the part of the balloon 1 that does not reach the gravity center P1 of the tubular object 10 becomes the wing-shaped portion 3. As a result, the balloon 1 can be folded with arranging the projecting portion 2 between a plurality of wing-shaped portion 3 and controlling the position of the projecting portion 2. In addition, since the projecting portion 2 is arranged between a plurality of wing-shaped portion 3 and the wing-shaped portion 3 is wound and folded with covering the projecting portion 2, the balloon catheter can be successfully inserted into a living body lumen such as a blood vessel.

The width W1 of the groove portion 20 is preferably larger than the width W2 of the projecting portion 2, and the depth d1 of the groove portion 20 is preferably smaller than the height H1 of the projecting portion 2. The width W1 of the groove portion 20 is preferably 1.1 times or more, more preferably 1.3 times or more, and even more preferably 1.5 times or more to the width W2 of the projecting portion 2. In addition, the depth d1 of the groove portion 20 is preferably 0.95 times or less, more preferably 0.9 times or less, and even ore preferably 0.85 times or less to the height H1 of the projecting portion 2. When the lower limit value of the ratio of the width W1 of the groove portion 20 to the width W2 of the projecting portion 2 and the upper limit value of the ratio of the width W1 of the groove portion 20 to the width W2 of the projecting portion 2 is adjusted to the above ranges, the apex part 2a of the projecting portion 2 is easily contacted with the inside of the groove portion 20 in the apex-positioning step and thus the efficiency of the apex-pressing step can be improved. In addition, the upper limit value of the ratio of the width W1 of the groove portion 20 to the width W2 of the projecting portion 2 is not particularly restricted, and the ratio can be adjusted to, for example, 10 times or less, 7 times or less, or 5 times or less. The lower limit value of the width W1 of the groove portion 20 to the width W2 of the projecting portion 2 is also not particularly restricted, and may be adjusted to, for example, 0.5 times or more, 0.6 times or more, or 0.7 times or more.

FIG. 5 shows a cross-sectional view in the projecting portion both sides-pressing step of the first method for producing a balloon catheter in accordance with the other embodiment of the present invention.

The method preferably comprises the projecting portion both sides-pressing step to press both sides of the projecting portion 2 on the cross-section perpendicular to the distal-proximal direction to the inside of the tubular object 10 after the balloon placement step. For example, a plurality of the projection shape part 12 that can be embedded from the outside into the inside of the tubular object 10 is formed on the inner surface of the tubular object 10, two of the projection shape part 12 are respectively contacted with the both sides of the projecting portion 2, and then the projection shape parts 12 are transferred into the inside of the tubular object 10 as shown in FIG. 5; or discharge ports for fluid such as air are provided in the tubular object 10 at both side portions of the projecting portion 2, and compressed air or the like is discharged from the two discharge ports toward both sides of the projecting portion 2 in order to press both sides of the projecting portion 2 to the inside of the tubular object 10. When both sides of the projecting portion 2 are pressed to the inside of the tubular object 10, the projecting portion 2 is hardly leaned to the circling direction of the balloon 1 and easily gets close to the gravity center P1 of the tubular object 10 in a standing position. When the folded balloon 1 is inflated while the projecting portion 2 stands during the use of the balloon catheter, the projecting portion 2 perpendicularly contacts with a lesion, the inner pressure of the balloon 1 can efficiently transmit to the lesion by perpendicularly contacting the projecting portion 2 with a lesion and thus high expansive force can be exerted.

It is preferred as shown in FIG. 1 that the tubular object 10 internally has a plurality of groove portion 20 extending in the distal-proximal direction at inside the tubular object 10, the width W1 of the groove portion 20 is smaller than the width W2 of the projecting portion 2, and the depth d1 of the groove portion 20 is larger than the height H1 of the projecting portion 2. It is preferred that the method preferably comprises the apex-positioning step to position the projecting portion 2 inside of the groove portion 20 after the balloon placement step, and the groove portion 20 is placed inside of the mean circle C1. When the tubular object 10 internally has a plurality of the groove portion 20, the width W1 of the groove portion 20 is smaller than the width W2 of the projecting portion 2 and the depth d1 of the groove portion 20 is larger than the height H1 of the projecting portion 2, it becomes easier that both side portions of the projecting portion 2 are contacted with the groove portion 20 and depressed. As a result, the balloon 1 can be folded while the apex part 2a of the projecting portion 2 is hardly crushed.

When the groove portion 20 is located inside of the mean circle C1, the projecting portion 2 positioned near the gravity center P1 of the tubular object 10 reaches the gravity center P1 of the tubular object 10 in advance of the other part of the tubular object 10 in the case where the inside of the balloon 1 is deflated in the balloon deflating step, and the part of the balloon 1 that does not reach the gravity center P1 of the tubular object 10 becomes the wing-shaped portion 3. Thus, the projecting portion 2 is located between a plurality of the wing-shaped portion 3 in the balloon 1 in the deflated state, and the balloon 1 can be folded while the position of the projecting portion 2 is controlled. In addition, since the projecting portion 2 is positioned between a plurality of wing-shaped portion 3 and the wing-shaped portion 3 is wound and folded with covering the projecting portion 2, the projecting portion 2 is hardly crushed.

The width W1 of the groove portion 20 is preferably smaller than the width W2 of the projecting portion 2, and the depth d1 of the groove portion 20 is preferably larger than the height H1 of the projecting portion 2. The width W1 of the groove portion 20 is preferably 0.95 times or less, more preferably 0.9 times or less, and even more preferably 0.85 times or less to the width W2 of the projecting portion 2. The depth d1 of the groove portion 20 is preferably 1.1 times or more, more preferably 1.3 times or more, and even more preferably 1.5 times or more to the height H1 of the projecting portion 2. When the upper limit value of the ratio of the width W1 of the groove portion 20 to the width W2 of the projecting portion 2 and the lower limit value of the ratio of the width W1 of the groove portion 20 to the width W2 of the projecting portion 2 are respectively adjusted to the above ranges, both sides of the projecting portion 2 can be easily contacted with the groove portion 20 in the projecting portion-positioning step and thus the projecting portion both sides-pressing step can be efficiently carried out. The lower limit value of the ratio of the width W1 of the groove portion 20 to the width W2 of the projecting portion 2 is not particularly restricted and may be adjusted to, for example, 0.5 times or more, 0.6 times or more, or 0.7 times or more. In addition, the upper limit value of the ratio of the width W1 of the groove portion 20 to the width W2 of the projecting portion 2 is also not particularly restricted, and can be adjusted to, for example, 10 times or less, 7 times or less, or 5 times or less.

The width W1 of the groove portion 20 may be larger than the width W2 of the projecting portion 2, and the depth d1 of the groove portion 20 may be larger than the height H1 of the projecting portion 2. When the width W1 of the groove portion 20 is larger than the width W2 of the projecting portion 2 and the depth d1 of the groove portion 20 is larger than the height H1 of the projecting portion 2, the projecting portion 2 can be easily positioned inside of the groove portion 20.

Next, the second method for producing a balloon catheter according to the present invention is described. The description of the part overlapping with the above description is omitted in the description of the second method for producing a balloon catheter.

FIG. 6 shows a cross-sectional view in the balloon placement step of the second method for producing a balloon catheter as the embodiment of the present invention, and FIG. 7 shows a cross-sectional view in the balloon deflating step. The second method for producing a balloon catheter is a method for producing a balloon catheter comprising a shaft and the balloon 1, wherein the shaft extends in a distal-proximal direction, and the balloon 1 provided on a distal side of the shaft and has a projecting portion 2 on an outer surface. The method comprises the tubular object preparing step to prepare the tubular object 10 internally having the space 11 extending in the distal-proximal direction and having a plurality of the groove portion 20 extending in the distal-proximal direction, the balloon preparing step to prepare the balloon 1, the balloon placement step to placing the balloon 1 in the tubular object 10 and inflate the balloon 1 by pressurizing the inside of the balloon 1, and the balloon deflating step to deflate the balloon 1 and form the wing-shaped portion 3 by depressurizing the inside of the balloon 1.

The tubular object 10 internally having the space 11 extending in the distal-proximal direction and a plurality of groove portion 20 extending in the distal-proximal direction is prepared in the tubular object preparing step. The balloon placement step to placing the balloon 1 in the tubular object 10 and inflate the balloon 1 by pressurizing the inside of the balloon 1 as shown in FIG. 6 is carried out after the tubular object preparing step.

The projecting portion 2 is placed on the inside of the mean circle C1 centered at the gravity center P1 of the tubular object 10, and the radius of the mean circle C1 is an average value of the shortest distance D1 from the gravity center P1 of the tubular object 10 to the inside surface P2 of the tubular object 10 and the longest distance D2 from the gravity center P1 of the tubular object 10 to the inside surface P3 of the tubular object 10 on a cross-section perpendicular to the distal-proximal direction of the tubular object 10 in the balloon placement step as shown in FIG. 6.

The projecting portion 2 is positioned inside of the groove portion 20 in the balloon placement step. When the projecting portion 2 is positioned inside of the groove portion 20, the projecting portion 2 is hardly pressed on the inner surface of the tubular object 10 in the case where the inside of the balloon 1 is pressurized in the balloon placement step, and thus the projecting portion 2 is prevented from being pressed and crushed. For example, the projecting portion 2 is inserted into the inside of the groove portion 20 by pressurizing the inside of the balloon 1 in order to position the projecting portion 2 inside of the groove portion 20.

The balloon deflating step to deflate the balloon 1 and form the wing-shaped portion 3 by depressurizing the inside of the balloon 1 as shown in FIG. 7 is carried out after the balloon placement step.

The difference between the width W1 of the groove portion 20 and the width W2 of the projecting portion 2 is preferably 50% or lower, comprising 0%, of the width W2 of the projecting portion 2 on the cross-section perpendicular to the distal-proximal direction of the tubular object 10 as shown in FIG. 6. When the difference between the width W1 of the groove portion 20 and the width W2 of the projecting portion 2 is 50% or lower, comprising 0%, of the width W2 of the projecting portion 2, the projecting portion 2 is maintained by the groove portion 20 with a certain amount of force, and the position of the projecting portion 2 can be controlled in the balloon deflating step. The phrase, "the difference between the width W1 of the groove portion 20 and the width W2 of the projecting portion 2 is 0% of the width W2 of the projecting portion 2", means that the width W1 of the groove portion 20 is the same as the width W2 of the projecting portion 2.

When the difference between the width W1 of the groove portion 20 and the width W2 of the projecting portion 2 is 50% or lower, comprising 0%, of the width W2 of the projecting portion 2, the balloon 1 can be folded with controlling the position of the projecting portion 2 by decreasing the pressure of the inside of the balloon 1, deflating the part of the balloon 1 that is not retained with the tubular object 10 to start the formation of the wing-shaped portion 3, increasing the power to draw the projecting portion 2 into the inside of the balloon 1 with decreasing the pressure of the inside of the balloon 1, and departing the projecting portion 2 from the groove portion 20 when the force to draw the balloon 1 to the inside become more than the force of the groove portion 20 to retain the projecting portion 2 in the balloon deflating step.

The difference between the width W1 of the groove portion 20 and the width W2 of the projecting portion 2 on the cross-section perpendicular to the distal-proximal direction of the tubular object 10 is preferably 50% or lower, more preferably 45% or lower, and even more preferably 40% or lower of the width W2 of the projecting portion 2. When the upper limit value of the difference between the width W1 of the groove portion 20 and the width W2 of the projecting portion 2 is adjusted to the above range, the position of the projecting portion 2 can be controlled more easily in the case where the balloon 1 is folded by increasing the force of the groove portion 20 to retain the projecting portion 2 in the balloon deflating step. In addition, the difference between the width W1 of the groove portion 20 and the width W2 of the projecting portion 2 is preferably 3% or more, more preferably 5% or more, and even more preferably 10% or more of the width W2 of the projecting portion 2. When the lower limit value of the difference between the width W1 of the groove portion 20 and the width W2 of the projecting portion 2 is adjusted to the above range, it becomes easier to position the projecting portion 2 inside of the groove portion 20 in the balloon placement step.

The width W1 of the groove portion 20 may be larger or smaller than the width W2 of the projecting portion 2 in the cross section perpendicular to the distal-proximal direction of the tubular object 10. When the width W1 of the groove portion 20 is smaller than the width W2 of the projecting portion 20 and the projecting portion 2 is positioned inside of the groove portion 20, the entire projecting portion 2 does not fit into the inside of the groove portion 20 and only a part of the projecting portion 2 sticks into the groove portion 20. As a result, the groove portion 20 can retain the projecting portion 2, and thus the position of the projecting portion 2 can be controlled in the case where the balloon 1 is folded.

The groove portion 20 is preferably located inside of the mean circle C1 as shown in FIG. 6. When the groove portion 20 is located inside of the mean circle C1, the position of the projecting portion 2 can be controlled in the balloon deflating step.

The number of the protruding portions 2 is preferably two or more, and the number of the groove portion 20 is preferably the same as the number of the protruding portion 2. When both of the number of the protruding portion 2 and the number of groove portion 20 are plural and the same each other, the balloon catheter having the protruding portion 2 that can sufficiently dilate a narrowing part at a calcified lesion and an ISR lesion can be produced. In addition, it can be prevented that the protruding portion 2 is pressed on the inner surface of the tubular object 10 and thus crushed during the production of a balloon catheter.

The protruding portion 2 is preferably composed of the same material as the main body of the balloon 1. When the protruding portion 2 is composed of the same material as the main body of the balloon 1, the joint strength between the main body of the balloon 1 and the projecting portion 2 can be increased.

It is preferred that the main body of the balloon 1 and the projecting portion 2 are integrally formed. When the main body of the balloon 1 and the projecting portion 2 are integrally formed, the joint strength between the main body of the balloon 1 and the projecting portion 2 can be further increased. In addition, since a step to bond the projecting portion 2 on the main body of the balloon 1 is not needed, the time for the forming the balloon 1 can be shortened and thus the production efficiency can be improved.

The balloon 1 preferably has hydrophilic coating on the outer surface, and the method preferably comprises the coating removing step to remove the hydrophilic coating on the apex part 2a of the projecting portion 2. When hydrophilic coating is applied to the outer surface of the balloon 1 and the hydrophilic coating on the apex part 2a of the projecting portion 2 is removed, the balloon catheter can be easily handled, since the apex part 2a of the projecting portion 2 is easily gotten stuck with a lesion due to low sliding performance and the sliding performance of the outer surface of the balloon 1 other than the apex part 2a of the projecting portion 2 is high due to the hydrophilic coating.

The coating removing step is preferably carried out after the balloon placement step, and the outer surface of the projecting portion 2 is preferably contacted with the inner surface of the tubular object 10 by sliding the balloon 1 in the distal-proximal direction in the coating removing step. In other words, the hydrophilic coating on the outer surface of the projecting portion 2 is preferably removed by sliding the hydrophilic coating on the outer surface of the projecting portion 2 with contacting the hydrophilic coating with the inner surface of the tubular object 10. When the coating removing step is carried out by sliding the balloon 1 in the distal-proximal direction and contacting the outer surface of the projecting portion 2 with the inner surface of the tubular object 10, the coating removing step can be carried out with an easy procedure with positioning the balloon 1 in the tubular object 10. Thus, the production efficiency of the balloon catheter can be improved.

The tubular object 10 preferably has the groove portion 20 extending in the distal-proximal direction, and the projecting portion 2 is preferably positioned inside of the groove portion 20. In addition, the outer surface of the projecting portion 2 is preferably contacted with the inner surface of the groove portion 20 by sliding the balloon 1 in the distal-proximal direction in the coating removing step. When the coating removing step is carried out by contacting the outer surface of the projecting portion 2 with the inner surface of the groove portion 20, the entire projecting portion 2 is easily contacted with the inner surface of the groove portion 20. Thus, the hydrophilic coating on the outer surface of the projecting portion 2 can be efficiently removed.

The average surface roughness Rz of the inner surface part of the tubular object 10 that is contacted with the outer surface of the projecting portion 2 is preferably higher than that of the other part. When the average surface roughness Rz of the inner surface part of the tubular object 10 that is contacted with the outer surface of the projecting portion 2 is higher than that of the other part, the hydrophilic coating on the outer surface of the projecting portion 2 can be efficiently removed but the hydrophilic coating on the outer surface of the balloon 1 other than the projecting portion 2 is hardly removed. As a result, the balloon catheter having the projecting portion 2 of which surface sliding performance is low can be easily produced.

As described above, the first method for producing a balloon catheter is characterized in that the balloon catheter comprises a shaft and a balloon, the shaft extends in a distal-proximal direction, and the balloon provided on a distal side of the shaft and has a projecting portion on an outer surface, and the method comprises tubular object preparing step to prepare a tubular object internally having a space extending in the distal-proximal direction, balloon preparing step to prepare the balloon, balloon placement step to placing the balloon in the tubular object and inflate the balloon by pressurizing an inside of the balloon, and balloon deflating step to deflate the balloon and form a wing-shaped portion by depressurizing the inside of the balloon, wherein the projecting portion is placed on the inside of a mean circle centered at a gravity center of the tubular object, and a radius of the mean circle is an average value of a shortest distance from the gravity center of the tubular object to an inside surface of the tubular object and a longest distance from the gravity center of the tubular object to the inside surface of the tubular object on a cross-section perpendicular to the distal-proximal direction of the tubular object in the balloon placement step. The second method for producing a balloon catheter is characterized in that the balloon catheter comprises a shaft and a balloon, the shaft extends in a distal-proximal direction, and the balloon provided on a distal side of the shaft and has a projecting portion on an outer surface, and the method comprises tubular object preparing step to prepare a tubular object internally having a space extending in the distal-proximal direction and having a plurality of groove portions extending in the distal-proximal direction, balloon preparing step to prepare the balloon, balloon placement step to placing the balloon in the tubular object and inflate the balloon by pressurizing an inside of the balloon, and balloon deflating step to deflate the balloon and form a wing-shaped portion by depressurizing the inside of the balloon, wherein the projecting portion is placed on the inside of a mean circle centered at a gravity center of the tubular object, and a radius of the mean circle is an average value of a shortest distance from the gravity center of the tubular object to an inside surface of the tubular object and a longest distance from the gravity center of the tubular object to the inside surface of the tubular object on a cross-section perpendicular to the distal-proximal direction of the tubular object in the balloon placement step, and wherein the projecting portion is positioned inside of the groove portion in the balloon placement step. When the projecting portion is placed on the inside of a mean circle centered at a gravity center of the tubular object, and a radius of the mean circle is an average value of a shortest distance from the gravity center of the tubular object to an inside surface of the tubular object and a longest distance from the gravity center of the tubular object to the inside surface of the tubular object on a cross-section perpendicular to the distal-proximal direction of the tubular object in the balloon placement step to placing the balloon in the tubular object and inflate the balloon by pressurizing an inside of the balloon, the balloon can be folded while the projecting portion is hardly crushed and the position of the projecting portion is controlled.

The present application claims the benefit of the priority date of Japanese patent application No. 2019-163858 filed on Sep. 9, 2019. All of the contents of the Japanese patent application No. 2019-163858 filed on Sep. 9, 2019, are incorporated by reference herein.

DESCRIPTION OF REFERENCE SIGNS

1: Balloon
2: Projecting portion
2a: Apex part of projecting portion
3: Wing-shaped portion
10: Tubular object
11: Space portion
20: Groove portion
P1: Gravity center of tubular object P2: Point on inner surface of tubular object to which distance from gravity center of tubular object is the shortest
P3: Point on inner surface of tubular object to which distance from gravity center of tubular object is the longest
D1: Distance between gravity center of tubular object and point on inner surface of tubular object to which distance from gravity center of tubular object is the shortest
D2: Distance between gravity center of tubular object and point on inner surface of tubular object to which distance from gravity center of tubular object is the longest
C1: Mean circle having radius of average value of distance between gravity center of tubular object and point on inner surface of tubular object to which distance from gravity center of tubular object is the shortest and distance between gravity center of tubular object and point on inner surface to which distance from gravity center of tubular object is the longest
L0: Straight line through gravity center of tubular object and apex part of projecting portion before rotating balloon in one direction
L1: Straight line through gravity center of tubular object and apex part of projecting portion after rotating balloon in one direction
W1: Width of groove portion
W2: Width of projecting portion
D1: Depth of groove portion
H1: Height of projecting portion

The invention claimed is:
1. A method for producing a balloon catheter, comprising:
a balloon placement step to place a balloon catheter in an inner space of a tubular object and inflate a balloon by pressurizing an inside of the balloon, the balloon catheter having a shaft extending in a distal-proximal direction and the balloon provided on a distal side of the shaft and having a projecting portion on an outer surface, and the inner space extending in the distal-proximal direction, and
a balloon deflating step to deflate the balloon and form a wing-shaped portion by depressurizing the inside of the balloon,
wherein on a single cross-section of the tubular object perpendicular to the distal-proximal direction, the inner space of the tubular object has a shortest portion at which a distance from a center of a figure with an outer shape of the inner space of the tubular object as an outline to an inner surface of the tubular object is shortest and a longest portion at which a distance from the center of the figure with the outer shape of the inner space of the tubular object as the outline to the inner surface of the tubular object is longest,
in the balloon placement step and before the balloon deflating step, on the same cross-section, the projecting portion is placed on the inside of a mean circle centered at the center of the figure with the outer shape of the inner space of the tubular object as the outline, and a radius of the mean circle is an average value ((D1+D2)/2) of a shortest distance (D1) from the center of the figure with the outer shape of the inner space of the tubular object as the outline to an inner surface of the tubular object at the shortest portion and a longest distance (D2) from the center of the figure with the outer shape of the inner space of the tubular object as the outline to the inner surface of the tubular object at the longest portion.

2. The method for producing a balloon catheter according to claim 1, further comprising an apex-pressing step to press an apex part of the projecting portion toward the inner surface of the inner space of the tubular object after the balloon placement step and before the balloon deflating step.

3. The method for producing a balloon catheter according to claim 2, wherein the balloon has a plurality of the projecting portions, and in the apex-pressing step, the balloon is rotated in the inner space of the tubular object so that a straight line through the center of the figure with the outer shape of the inner space of the tubular object as the outline and the apex part of the projecting portion turns round an axis direction of the tubular object and rotation directions of the all straight lines through the center of the figure with the outer shape of the inner space of the tubular object as the outline and the apex parts of the projecting portions are the same on the cross-section perpendicular to the distal-proximal direction of the tubular object.

4. The method for producing a balloon catheter according to claim 2, wherein the tubular object has a plurality of groove portions extending in the distal-proximal direction in the inner space, a width of the groove portion is larger than a width of the projecting portion, and a depth of the groove portion is smaller than a height of the projecting portion, and the groove portion is positioned within the mean circle, and wherein the method further comprises an apex-positioning step to position the projecting portion inside of the groove portion after the balloon placement step.

5. The method for producing a balloon catheter according to claim 1, wherein the projecting portion comprise two outer surfaces, and both of the two outer surfaces of the projecting portion are pressed toward the inner surface of the inner space of the tubular object on the cross-section perpendicular to the distal-proximal direction after the balloon placement step.

6. The method for producing a balloon catheter according to claim 5, wherein the tubular object has a plurality of groove portions extending in the distal-proximal direction in the inner space, a width of the groove portion is smaller than a width of the projecting portion, and a depth of the groove portion is larger than a height of the projecting portion, and the groove portion is positioned within the mean circle, and wherein the method further comprises an apex-positioning step to position the apex part inside of the groove portion after the balloon placement step.

7. A method for producing a balloon catheter, comprising:
a balloon placement step to place a balloon catheter in an inner space of a tubular object and inflate a balloon by pressurizing an inside of the balloon, the balloon catheter having a shaft extending in a distal-proximal direction and the balloon provided on a distal side of the shaft and having a projecting portion on an outer surface, and the inner space extending in the distal-proximal direction and having a plurality of groove portions extending in the distal-proximal direction, and a balloon deflating step to deflate the balloon and form a wing-shaped portion by depressurizing the inside of the balloon, wherein on a single cross-section of the tubular object perpendicular to the distal-proximal direction, the inner space of the tubular object has a shortest portion at which a distance from a center of a figure with an outer shape of the inner space of the tubular object as an outline to an inner surface of the tubular object is shortest and a longest portion at which a distance from the center of the figure with the outer shape of the inner space of the tubular object as the outline to the inner surface of the tubular object is longest, in the balloon placement step and before the balloon deflating step, on the same cross-section, the projecting portion is placed on the inside of a mean circle centered at the center of the figure with the outer shape of the inner space of the tubular object as the outline, and a radius of the mean circle is an average value ($(D1+D2)/2$) of a shortest distance ($D1$) from the center of the figure with the outer shape of the inner space of the tubular object as the outline to an inner surface of the tubular object at the shortest portion and a longest distance ($D2$) from the center of the figure with the outer shape of the inner space of the tubular object as the outline to the inner surface of the tubular object at the longest portion, and wherein the projecting portion is positioned inside of the groove portion in the balloon placement step.

8. The method for producing a balloon catheter according to claim 7, wherein a difference between a width of the groove portion and a width of the projecting portion is 0% to 50% of the width of the projecting portion on the cross-section perpendicular to the distal-proximal direction of the tubular object.

9. The method for producing a balloon catheter according to claim 7, wherein the groove portion is positioned inside of the mean circle.

10. The method for producing a balloon catheter according to claim 7, wherein the number of the projecting portion is two or more, and the number of the groove portion is the same as the number of the projecting portion.

11. The method for producing a balloon catheter according to claim 1, wherein the projecting portion is composed of the same material of a main body of the balloon.

12. The method for producing a balloon catheter according to claim 1, wherein the balloon has hydrophilic coating on an outer surface, and the method further comprises a coating removing step to remove the hydrophilic coating on an apex part of the projecting portion.

13. The method for producing a balloon catheter according to claim 12, wherein the coating removing step is carried out after the balloon placement step, and the hydrophilic coating is removed from the apex part of the projecting portion by sliding the balloon in the distal-proximal direction so that an outer surface of the projecting portion contacts with the inner surface of the tubular object in the coating removing step.

14. The method for producing a balloon catheter according to claim 7, wherein the projecting portion is composed of the same material of a main body of the balloon.

15. The method for producing a balloon catheter according to claim 7, wherein the balloon has hydrophilic coating on an outer surface, and the method further comprises a coating removing step to remove the hydrophilic coating on an apex part of the projecting portion.

16. The method for producing a balloon catheter according to claim 15, wherein the coating removing step is carried out after the balloon placement step, and the hydrophilic coating is removed from the apex part of the projecting portion by sliding the balloon in the distal-proximal direction so that an outer surface of the projecting portion contacts with the inner surface of the tubular object in the coating removing step.

17. The method for producing a balloon catheter according to claim 1, wherein in the balloon placement step and before the balloon deflating step, the projecting portion is placed on the inside of the mean circle centered at the center of the figure, and at least a part of the balloon is placed on the outside of the mean circle.

18. The method for producing a balloon catheter according to claim 7, wherein in the balloon placement step and before the balloon deflating step, the projecting portion is placed on the inside of the mean circle centered at the center of the figure, and at least a part of the balloon is placed on the outside of the mean circle.

19. The method for producing a balloon catheter according to claim 1, wherein in the balloon placement step and before the balloon deflating step, the balloon catheter is placed in the inner space of the tubular object so that the projecting portion is placed on the inside of the mean circle and at a position closer to the center of the figure than a part of the balloon, and in the balloon deflating step, the inside of the balloon is depressurized so that the projecting portion moves toward the center of the figure in advance of the part of the balloon, whereby forming the wing-shaped portion.

20. The method for producing a balloon catheter according to claim 7, wherein in the balloon placement step and before the balloon deflating step, the balloon catheter is placed in the inner space of the tubular object so that the projecting portion is placed on the inside of the mean circle and at a position closer to the center of the figure than a part of the balloon, and in the balloon deflating step, the inside of the balloon is depressurized so that the projecting portion moves toward the center of the figure in advance of the part of the balloon, whereby forming the wing-shaped portion.

* * * * *